(12) United States Patent
Smalldon

(10) Patent No.: US 7,955,552 B1
(45) Date of Patent: Jun. 7, 2011

(54) CAR FRESHENER SYSTEM AND ASSOCIATED METHOD

(76) Inventor: Bob Smalldon, Sunlakes, AZ (US)

( * ) Notice: Subject to any disclaimer, the term of this patent is extended or adjusted under 35 U.S.C. 154(b) by 457 days.

(21) Appl. No.: 12/069,166

(22) Filed: Feb. 8, 2008

(51) Int. Cl.
*A61L 9/00* (2006.01)
(52) U.S. Cl. ............... 422/5; 422/123; 239/34; 239/92; 239/123; 261/57; 261/58; 261/DIG. 88
(58) Field of Classification Search ............ 422/5, 123; 261/34, 57–58, DIG. 88; 239/92, 123, DIG. 88
See application file for complete search history.

(56) References Cited

U.S. PATENT DOCUMENTS

| | | | | |
|---|---|---|---|---|
| 4,095,307 | A | * | 6/1978 | Brubaker ................... 15/246.5 |
| 5,549,854 | A | * | 8/1996 | Hulthom et al. ............... 261/87 |
| 6,179,219 | B1 | * | 1/2001 | Lin ................................ 239/44 |
| 2005/0226788 | A1 | * | 10/2005 | Hrybyk et al. ............... 422/124 |

* cited by examiner

*Primary Examiner* — Walter D Griffin
*Assistant Examiner* — Christopher K VanDeusen

(57) ABSTRACT

A car freshener system includes a portable reservoir seated within the vehicle, a predetermined volume of a liquid air freshening compound housed within the reservoir, and a portable discharge casing disposed within the vehicle with a rotary discharging mechanism housed therein. The discharge casing includes an input port and an output port in fluid communication with the reservoir in such a manner that the liquid air freshening compound is caused to enter through the input port and travels along a unidirectional arcuate path defined along a major interior circumference of the discharge casing prior to exiting through the output port.

10 Claims, 4 Drawing Sheets

CAR FRESHENER SYSTEM AND ASSOCIATED METHOD

CROSS REFERENCE TO RELATED APPLICATIONS

Not Applicable.

STATEMENT REGARDING FEDERALLY SPONSORED RESEARCH OR DEVELOPMENT

Not Applicable.

REFERENCE TO A MICROFICHE APPENDIX

Not Applicable.

BACKGROUND OF THE INVENTION

1. Technical Field

This invention relates to air fresheners and, more particularly, to a car freshener system for effectively discharging a scent within a vehicle.

2. Prior Art

Closed vehicles, such as cars, vans, utility vehicles, trucks, boats with closed cabins, and the like, present an environment for their occupants that in some circumstances can be unpleasant. For example, even with a good ventilating system a closed road vehicle driven in heavy traffic or in an area with significant air pollution can become stuffy and malodorous. Many individuals, moreover, are used to aroma therapy in a room setting and would benefit from having aroma therapy readily available in a vehicle. Vehicle occupants are also prone to drowsiness, which is, of course, very undesirable and dangerous in the case of the driver.

The use of devices which emit pleasant odors inside an automobile with the intention of masking the bad smells that may arise in a closed compartment is nothing new. For example, relatively uncomplicated devices supplied with solids which sublimate on contact with the atmosphere have been used for many years, both in cars and in houses and places of work. A heat released vehicular air freshener has also been introduced in the prior art that includes a power unit for being releasably received in electrical communication with a vehicular cigarette lighter. Also included is a fragrance mechanism mounted on the power unit for dispensing an aroma when actuated. An actuation assembly includes a timer mechanism for actuating the fragrance mechanism for a predetermined amount of time when actuated.

Unfortunately, neither of the previous examples provides the vehicle operator with effective control over the amount of fragrance being emitted. Furthermore, these fragrance emitting means are constantly releasing chemicals, thus causing the fragrance dispenser to quickly lose its scent releasing capability. Thus the vehicle owner must frequently replace the fragrance dispenser. Over time this can become a rather expensive practice.

U.S. Pat. No. 6,938,833 to Chen discloses a vehicle air freshener that includes a bottle holding a color fluid and a volatile liquid perfume floating on the color fluid, a socket fastened to the bottle neck of the bottle to hold an absorptive core member that dissipates the volatile liquid perfume into air outside the bottle, a weight-attached ornament set in the volatile liquid perfume and the color fluid, a base fastened to the bottom side of the bottle and adapted to support the vehicle air freshener on a surface, and a bottle cap fastened to the bottle neck of the bottle around the socket. The bottle cap has a center through hole which receives the bottleneck of the bottle, and a plurality of wire holes for mounting cord members. Unfortunately, this prior art example operates automatically without any input from a user.

U.S. Pat. No. 6,179,219 to Lin discloses a vehicle air-freshener that includes a holder base for mounting inside a motor vehicle, a container body mounted on the holder base and holding a perfume, the container body having a recessed top side wall, and a top center through hole formed through the lowest area of the recessed top side wall for enabling the smell of the perfume to escape out of the container body into the air, a control ball moved in the recessed top side wall of the container body to close/open the top center through hole, and a perforated cap covered on the container body to hold the control ball in the recessed top side wall of the container body. Unfortunately, this prior art example is automatic and not operable at the user's whim.

U.S. Pat. No. 5,269,723 to Bender discloses a vehicle air freshener that is quickly and easily installable and removable from an outlet grille of the vehicle ventilating system. The air freshener includes a tube filled with a fragrance saturated absorbent material. The tube has a sufficiently small diameter to pass through the typical opening in a vehicle interior ventilation outlet grille, and includes a thin, elongate extension and handle which is wider than the grille opening, to preclude passage of the handle through the grille opening. The air freshener is initially provided with one or more sealed scent passages, which are punctured or otherwise removed to allow the scent or fragrance to escape the interior of the air freshener and mix with the air. After opening the scent passage seal, the air freshener is inserted into the ventilation grille opening and is prevented from falling into the ductwork of the ventilation system by the handle which is caught on the outside of the grille, thereby substantially concealing the air freshener. Any air flowing through the ventilation system will absorb the fragrance escaping from the opened scent passage and pass into the vehicle interior. The air freshener may be easily removed when the scent is depleted or no longer desired, by grasping the handle and withdrawing the air freshener from the duct and grille opening. At least the handle portion may be provided in different colors to closely match the colors of various ventilation grilles, in order to provide an unobtrusive appearance. Unfortunately, this prior art example this prior art example operates automatically without any input from a user.

Accordingly, the present invention is disclosed in order to overcome the above noted shortcomings. The car freshener system is convenient and easy to use, lightweight yet durable in design, and designed for effectively discharging a scent within a vehicle. The present invention is simple to use, inexpensive, and designed for many years of repeated use.

BRIEF SUMMARY OF THE INVENTION

In view of the foregoing background, it is therefore an object of the present invention to provide an apparatus for effectively discharging a scent within a vehicle. These and other objects, features, and advantages of the invention are provided by a car freshener system.

A car freshener system includes a portable reservoir seated within the vehicle, a predetermined volume of a liquid air freshening compound housed within the reservoir, and a portable discharge casing disposed within the vehicle with a rotary discharging mechanism housed therein. Such a discharge casing effectively includes a hollow chamber formed therein and in fluid communication with the input and output ports, a rod rotatably disposed within the chamber, and a mobile ring eccentrically disposed within the chamber. Such a primary mobile ring is provided with a plurality of linear fingers radially protruding outwardly from a perimeter thereof. The discharge casing further includes a plurality of rectilinear levers directly attached to the rod and terminating exterior of the mobile ring, a plurality of cranks pivotally attached to the fingers and the levers respectively, and a plurality of flaps pivotally coupled to the levers.

A traveling force of the liquid air freshening compound conveniently causes the mobile ring and the fingers to eccentrically rotate about the rod to thereby maintain outer edges of the flaps directly engaged with an interior surface of the chamber and effectively propel the liquid air freshening compound outward from the output port. The discharge casing includes an input port and an output port in fluid communication with the reservoir in such a manner that the liquid air freshening compound is caused to enter through the input port and travels along a unidirectional arcuate path defined along a major interior circumference of the discharge casing prior to exiting through the output port.

The levers are coextensively shaped and equidistantly spaced apart from a center of the rod so that the flaps advantageously maintain synchronous displacement within the chamber. Each of the cranks has axially opposed ends directly linked to corresponding ends of the levers and the fingers respectively, and each of the flaps extends from an outer perimeter of the mobile ring to the inner surface of the chamber. The levers are statically coupled to the rod and maintain a dynamic spatial relationship with the fingers when the mobile ring is eccentrically rotated about the rod for ensuring that the flaps maintain direct engagement with an inner surface of the chamber during rotary movement. Further, a controller is electrically coupled to the reservoir for controlling an operating speed of the rotary discharging mechanism.

A method for effectively discharging a scent within a vehicle includes the steps of: providing a portable reservoir seated within the vehicle; providing a predetermined volume of a liquid air freshening compound housed within the reservoir; providing a portable discharge casing disposed within the vehicle and including an input port and an output port in fluid communication with the reservoir; providing a rotary discharging mechanism housed within the casing; providing a controller electrically coupled to the reservoir for controlling an operating speed of the rotary discharging mechanism; and the liquid air freshening compound entering through the input port and traveling along a unidirectional arcuate path defined along a major interior circumference of the discharge casing prior to exiting through the output port.

The method further includes the steps of: providing a hollow chamber formed within the casing; providing a rod rotatably disposed within the chamber; providing a mobile ring eccentrically disposed within the chamber, the primary mobile ring being provided with a plurality of linear fingers radially protruding outwardly from a perimeter thereof; providing a plurality of rectilinear levers directly attached to the rod and terminating exterior of the mobile ring; providing a plurality of cranks pivotally attached to the fingers and the levers respectively; and providing a plurality of flaps pivotally coupled to the levers; a traveling force of the liquid air freshening compound causing the mobile ring and the fingers to eccentrically rotate about the rod; maintaining outer edges of the flaps directly engaged with an interior surface of the chamber; and propelling the liquid air freshening compound outward from the output port.

The method further includes the step of: synchronously displacing the flaps within the chamber; directly linking opposed ends of the cranks to corresponding ends of the levers and the fingers respectively; extending each of the flaps from and outer perimeter of the mobile ring to the inner surface of the chamber; statically coupling the levers to the rod; and maintaining a dynamic spatial relationship with the fingers when the mobile ring is eccentrically rotated about the rod for ensuring that the flaps maintain direct engagement with an inner surface of the chamber during rotary movement.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

It is noted the purpose of the foregoing abstract is to enable the U.S. Patent and Trademark Office and the public generally, especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

BRIEF DESCRIPTION OF THE SEVERAL
VIEWS OF THE DRAWING

The novel features believed to be characteristic of this invention are set forth with particularity in the appended claims. The invention itself, however, both as to its organization and method of operation, together with further objects and advantages thereof, may best be understood by reference to the following description taken in connection with the accompanying drawings in which:

DETAILED DESCRIPTION OF THE INVENTION

The present invention will now be described more fully hereinafter with reference to the accompanying drawings, in which a preferred embodiment of the invention is shown. This invention may, however, be embodied in many different forms and should not be construed as limited to the embodiment set forth herein. Rather, this embodiment is provided so that this application will be thorough and complete, and will fully convey the true scope of the invention to those skilled in the art. Like numbers refer to like elements throughout the figures.

Figure 1:
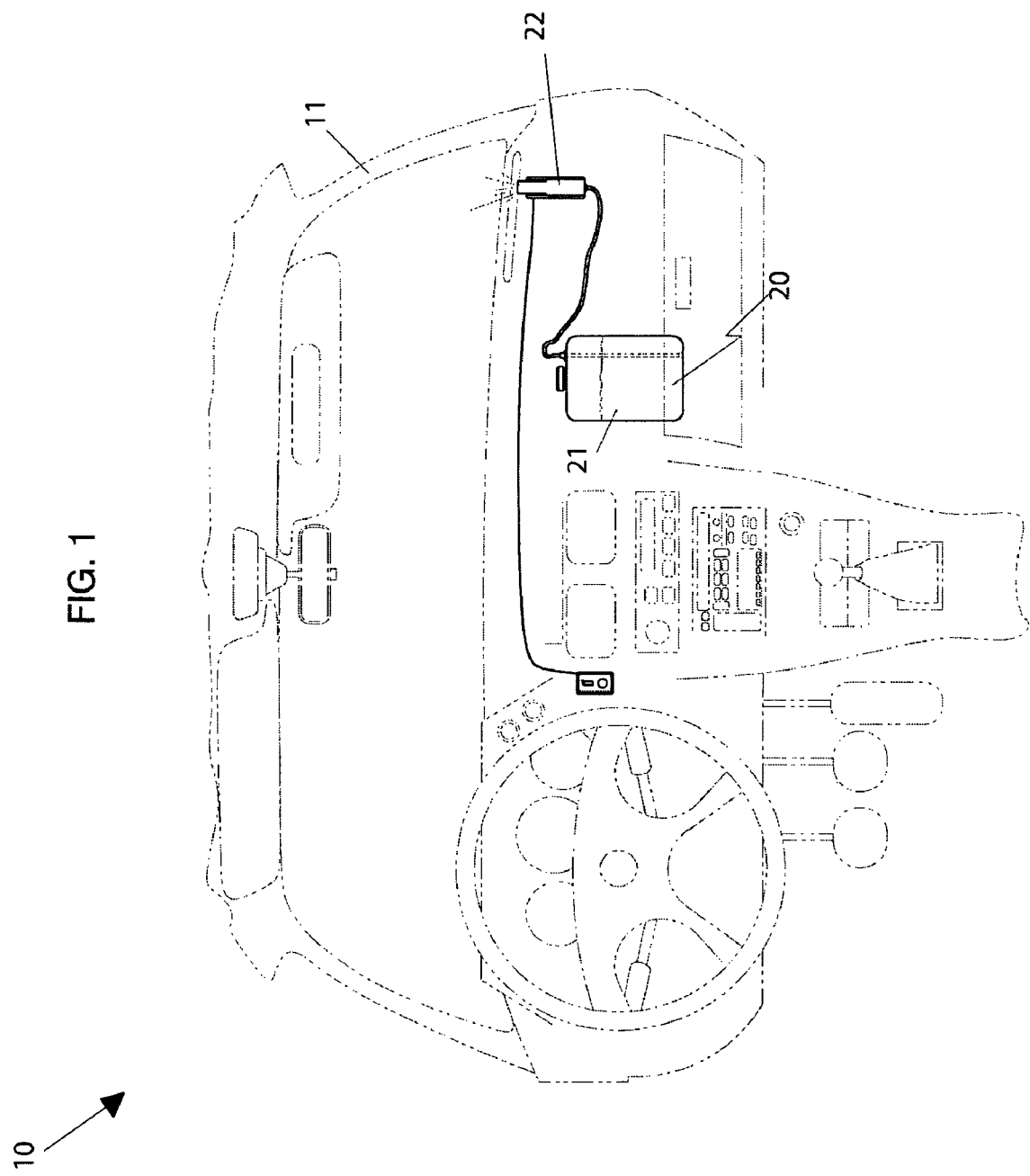
FIG. 1 is a perspective view showing a car freshener system installed within a vehicle, in accordance with the present invention.
Figure 2:
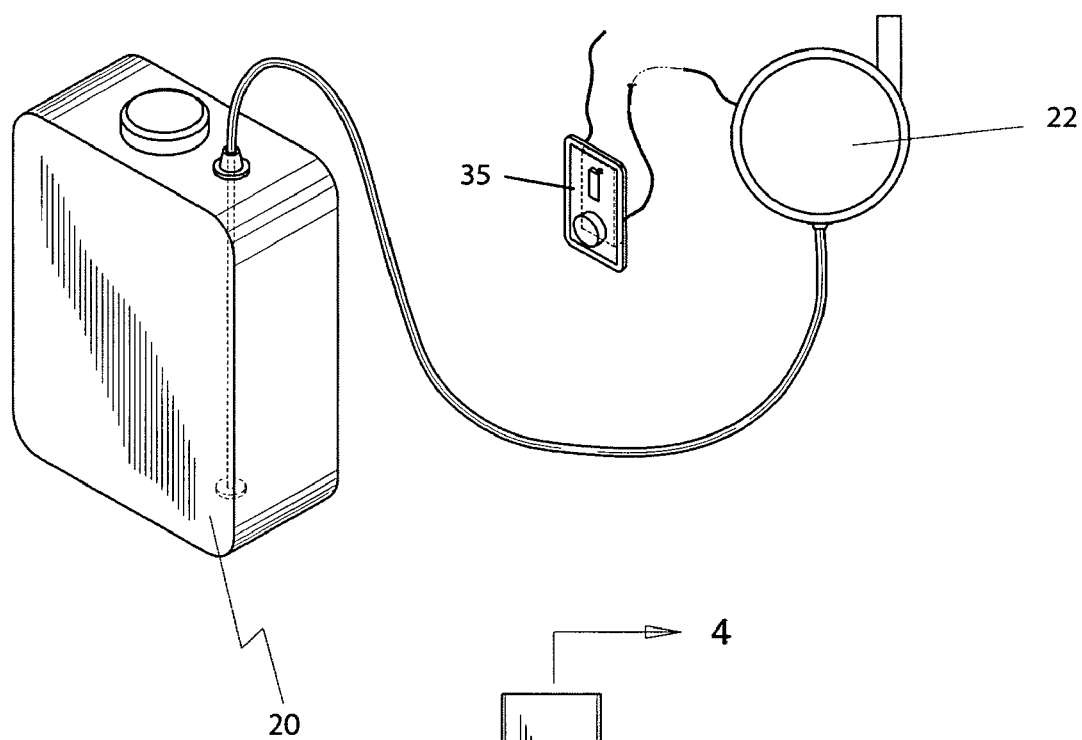
FIG. 2 is a perspective view of the car freshener system, in accordance with the present invention.
Figure 3:
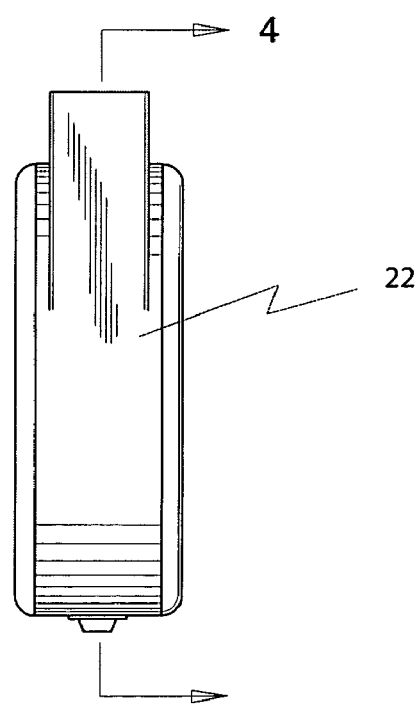
FIG. 3 is a side elevational view of the portable discharge casing, in accordance with the present invention.
Figure 4:
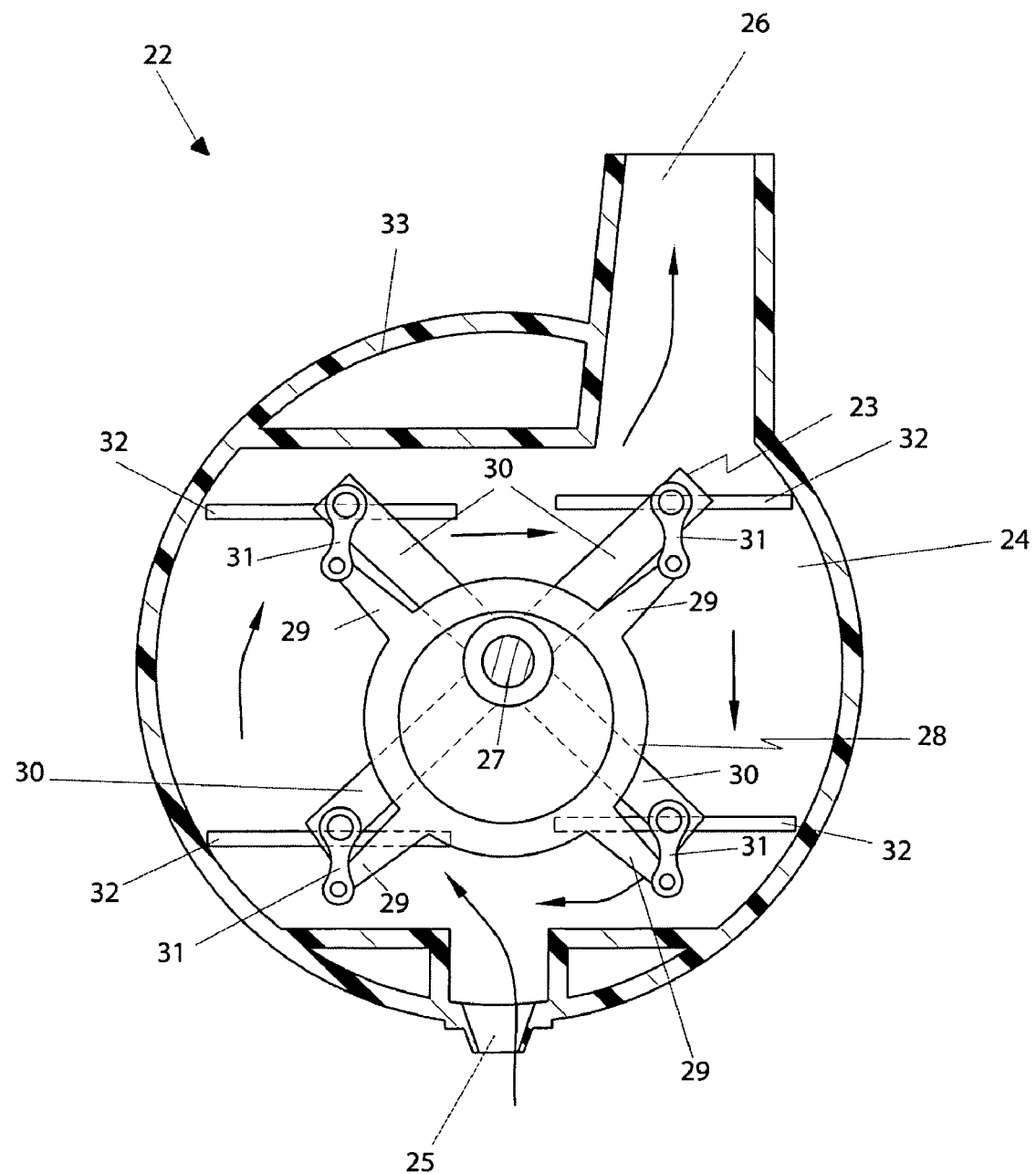
FIG. 4 is a cross sectional view of the car freshener system, taken along line 4-4, as seen in FIG. 3.
Figure 5:
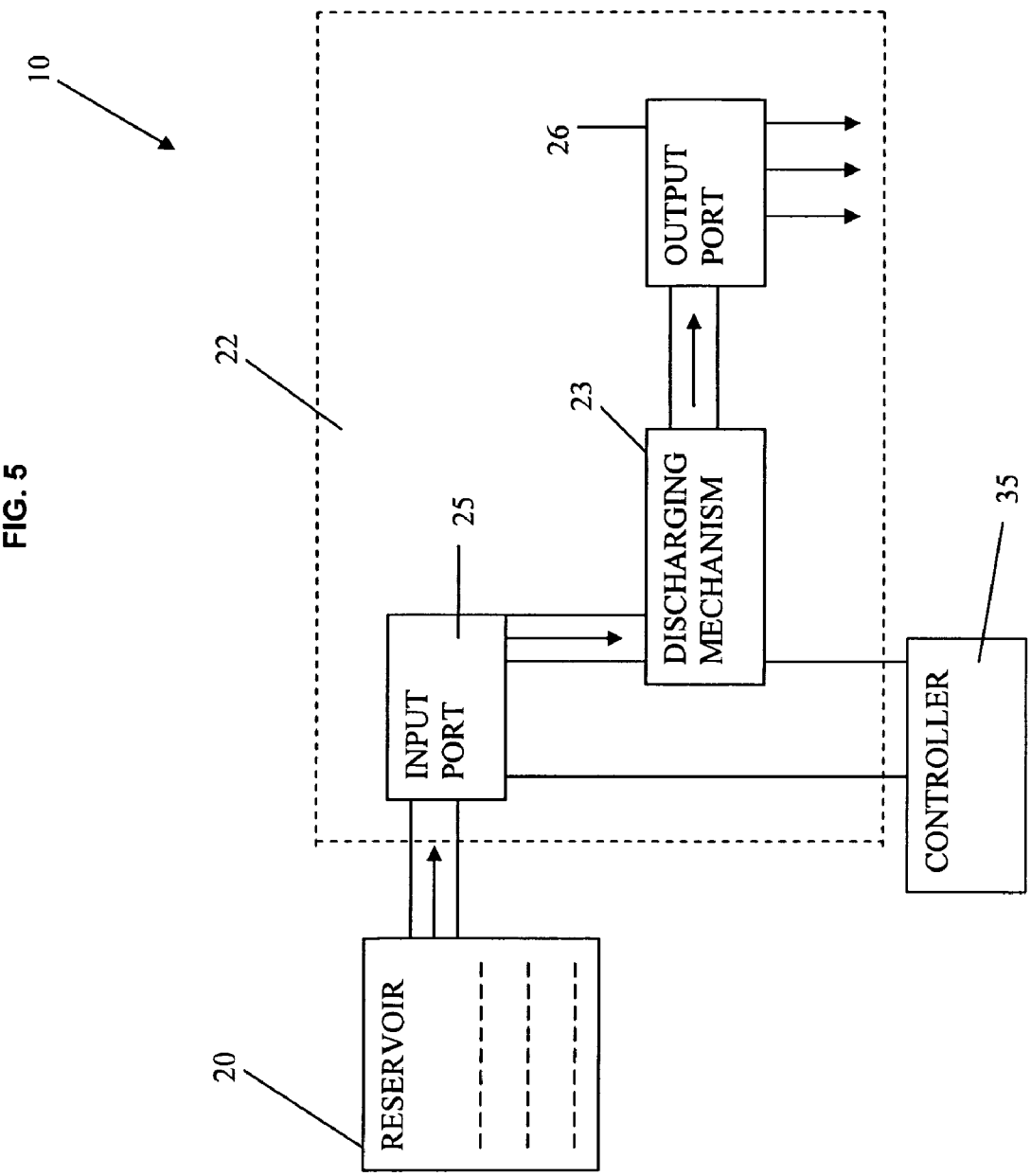
FIG. 5 is a schematic block diagram of the car freshener system, in accordance with the present invention.

The apparatus of this invention is referred to generally in FIGS. 1-5 by the reference numeral 10 and is intended to protect a car freshener system. It should be understood that the apparatus 10 may be used to freshen many different types of vehicles and should not be limited to use with only those types of vehicles mentioned herein.

Referring to FIGS. 1, 2, 3, 4 and 5, a car freshener system 10 includes a portable reservoir 20 seated within the vehicle 11, a predetermined volume of a liquid air freshening compound 21 housed within the reservoir 20, and a portable discharge casing 22 disposed within the vehicle 11 with a rotary discharging mechanism 23 housed therein. Such a discharge casing 22 includes a hollow chamber 24 formed therein and in fluid communication with input and output ports 25, 26, a rod 27 rotatably disposed within the chamber 24, and a mobile ring 28 eccentrically disposed within the chamber 24. Such a primary mobile ring 28 is provided with a plurality of linear fingers 29 radially protruding outwardly from a perimeter thereof. The discharge casing 22 further includes a plurality of rectilinear levers 30 directly attached, without the use of intervening elements, to the rod 27 and terminating exterior of the mobile ring 28, a plurality of cranks 31 pivotally attached to the fingers 29 and the levers 30 respectively, and a plurality of flaps 32 pivotally coupled to the levers 30. The discharge casing 22 receives the liquid air freshening compound 21 from the reservoir 20 and releases the scent through the output port 26, thereby refreshing a user vehicle 11.

A traveling force of the liquid air freshening compound 21 causes the mobile ring 28 and the fingers 29 to eccentrically rotate about the rod 27 to thereby maintain outer edges of the flaps 32 directly engaged, without the use of intervening elements, with an interior surface 33 of the chamber 24 and effectively propel the liquid air freshening compound 21 outward from the output port 26. The discharge casing 22 includes the input port and an output port 25, 26 in fluid communication with the reservoir 20 in such a manner that the liquid air freshening compound 21 is caused to enter through the input port 25 and travels along a unidirectional arcuate path defined along a major interior circumference of the discharge casing 22 prior to exiting through the output port 26.

The levers 30 are coextensively shaped and equidistantly spaced apart from a center of the rod 27 so that the flaps 32 maintain synchronous displacement within the chamber 24. Each of the cranks 31 has axially opposed ends directly linked, without the use of intervening elements, to corresponding ends of the levers 30 and the fingers 29 respectively, and each of the flaps 32 extends from an outer perimeter of the mobile ring 28 to the inner surface of the chamber 24. The levers 30 are statically coupled to the rod 27 and maintain a dynamic spatial relationship with the fingers 29 when the mobile ring 28 is eccentrically rotated about the rod 27 for ensuring that the flaps 32 maintain direct engagement with an inner surface of the chamber 24 during rotary movement. Further, a controller 35 is electrically coupled to the reservoir for controlling an operating speed of the rotary discharging mechanism. The controller 35 enables a user to refresh the user's vehicle 11 whenever needed by simple activation of the controller 25.

The system includes a refillable, capped receptacle that is located within the interior or below the vehicle hood. Of course, the receptacle may be positioned at any suitable and inconspicuous location within the vehicle, as is obvious to a person of ordinary skill in the art. Such a receptacle has an elongated conduit that is directly attached, without the use of intervening elements, to a discharge casing and discharge mechanism which effectively disperses a vaporous mist of freshener within the vehicle cabin. The mist is effectively dispensed through the vehicle's existing ventilation system. In an alternate embodiment, the system may include a plurality of discharge casings and mechanisms positioned about the vehicle cabin for effectively dispensing the fragrant mist.

The system is powered by a compact electric motor attached to a conventional pump (not shown) which is coupled to the reservoir and is activated via a push button switch (controller) that is positioned on the vehicle dashboard or center console for being conveniently and easily reached by the vehicle operator or their passenger. Of course, the fragrances offered for use with the system could be virtually endless, ranging from spicy, sensual musk and pleasing botanical scents to tasty fruit aromas and eye-opening environmental smells, as is obvious to a person of ordinary skill in the art. Furthermore, of course, the system could be incorporated into the design of newly manufactured automobiles, or produced in kit form to be retrofitted to existing vehicles, as is obvious to a person of ordinary skill in the art.

In use, the air freshener system for automobiles and the like is simple and straightforward to operate. First, the user selects the fragrance that appeals most to them and fills the receptacle with the desired scent. By way of example, a male consumer might enjoy a spicy musk, while a female may enjoy a fruity botanical scent. As desired, the user simply activates the system by depressing the operational button (controller) located on the vehicle dash or console to dispense a light burst of fragrance throughout the vehicle.

The present invention, as claimed, provides the unexpected and unpredictable benefit of a system that is convenient and easy to use, is durable in design, is versatile in its applications, and provides motorists with a simple and efficient means of infusing their vehicles with a light, clean scent. Such a system disburses a light burst of fragrant air freshener throughout the vehicle cabin, advantageously enabling consumers to enjoy a more pleasant environment during travel. By eliminating odors which result from cigarette or cigar smoke, traveling with pets, or eating in the car, as well as the stale, musty smell which can result when the vehicle is parked for an extended period, the present invention makes time spent on the road an enjoyable experience for both the driver and their passengers. With fragrances offered in a vast array of scents, there is certain to be a desired fragrance to appeal to virtually any automobile owner.

In use, a method for effectively discharging a scent within a vehicle includes the steps of: providing a portable reservoir 20 seated within the vehicle 11; providing a predetermined volume of a liquid air freshening compound 21 housed within the reservoir 20; providing a portable discharge casing 22 disposed within the vehicle 11 and including an input port and an output port 25, 26 in fluid communication with the reservoir 20; providing a rotary discharging mechanism 23 housed within the casing 22; providing a controller 35 electrically coupled to the reservoir 20 for controlling an operating speed of the rotary discharging mechanism 23; and the liquid air freshening compound 21 entering through the input port 25 and traveling along a unidirectional arcuate path defined along a major interior circumference of the discharge casing 22 prior to exiting through the output port 26.

In use, the method further includes the steps of: providing a hollow chamber 24 formed within the casing 22; providing a rod 27 rotatably disposed within the chamber 24; providing a mobile ring 28 eccentrically disposed within the chamber 24, the primary mobile ring 28 being provided with a plurality of linear fingers 29 radially protruding outwardly from a perimeter thereof; providing a plurality of rectilinear levers 30 directly attached, without the use of intervening elements, to the rod 27 and terminating exterior of the mobile ring 28; providing a plurality of cranks 31 pivotally attached to the fingers 29 and the levers 30 respectively; and providing a plurality of flaps 32 pivotally coupled to the levers 30; a traveling force of the liquid air freshening compound 21 causing the mobile ring 28 and the fingers 29 to eccentrically rotate about the rod 27; maintaining outer edges of the flaps 32 directly engaged, without the use of intervening elements, with an interior surface of the chamber 24; and propelling the liquid air freshening compound 21 outward from the output port 26.

In use, the method further includes the step of: synchronously displacing the flaps 32 within the chamber 24; directly linking, without the use of intervening elements, opposed ends of the cranks 31 to corresponding ends of the levers 30 and the fingers 29 respectively; extending each of the flaps 32 from and outer perimeter of the mobile ring 28 to the inner surface of the chamber 24; statically coupling the levers 30 to the rod 27; and maintaining a dynamic spatial relationship with the fingers 29 when the mobile ring 28 is eccentrically rotated about the rod 27 for ensuring that the flaps 32 maintain direct engagement with an inner surface of the chamber 24 during rotary movement.

While the invention has been described with respect to a certain specific embodiment, it will be appreciated that many modifications and changes may be made by those skilled in the art without departing from the spirit of the invention. It is intended, therefore, by the appended claims to cover all such modifications and changes as fall within the true spirit and scope of the invention.

In particular, with respect to the above description, it is to be realized that the optimum dimensional relationships for the parts of the present invention may include variations in size, materials, shape, form, function and manner of operation. The assembly and use of the present invention are deemed readily apparent and obvious to one skilled in the art.

What is claimed as new and what is desired to secure by Letters Patent of the United States is:

1. A car freshener system for effectively discharging a scent within a vehicle, said car freshener system comprising:
   a reservoir seated within the vehicle;
   a predetermined volume of a liquid air freshening compound housed within said reservoir;
   a discharge casing disposed within the vehicle and having a rotary discharging mechanism housed therein; and
   a controller electrically coupled to said reservoir for controlling an operating speed of said rotary discharging mechanism;
   wherein said discharge casing includes an input port and an output port in fluid communication with said reservoir in such a manner that said liquid air freshening compound is caused to enter through said input port and travels along an arcuate path defined along a major interior circumference of said discharge casing prior to exiting through said output port;
   wherein said input port is located along a peripheral edge of said discharge casing;
   wherein said discharge casing comprises:
   a hollow chamber formed therein and being in fluid communication with said input and output ports;
   a rod rotatably disposed within said chamber;
   a mobile ring eccentrically disposed within said chamber, said mobile ring being provided with a plurality of linear fingers radially protruding outwardly from a perimeter thereof;
   a plurality of rectilinear levers directly attached to said rod and terminating the exterior of said mobile ring;
   a plurality of cranks pivotally attached to said fingers and said levers respectively; and
   a plurality of flaps pivotally coupled to said levers;
   wherein a traveling force of said liquid air freshening compound causes said mobile ring and said fingers to eccentrically rotate about said rod to thereby maintain outer edges of said flaps directly engaged with an interior surface of said chamber and effectively propel said liquid air freshening compound outward from said output port.

2. The car freshener system of claim 1, wherein said levers are coextensively shaped and equidistantly spaced apart from a center of said rod so that said flaps maintain synchronous displacement within said chamber.

3. The car freshener system of claim 1, wherein each of said cranks have axially opposed ends directly linked to corresponding ends of said levers and said fingers respectively.

4. The car freshener system of claim 1, wherein each of said flaps extends from an outer perimeter of said mobile ring to said inner surface of said chamber.

5. The car freshener system of claim 1, wherein said levers are statically coupled to said rod and maintain a dynamic spatial relationship with said fingers when said mobile ring is eccentrically rotated about said rod for ensuring that said flaps maintain direct engagement with an inner surface of said chamber during rotary movement.

6. A method for effectively discharging a scent within a vehicle, said method comprising the steps of:
   a. providing a portable reservoir seated within the vehicle;
   b. providing a predetermined volume of a liquid air freshening compound housed within said reservoir;
   c. providing a portable discharge casing disposed within the vehicle and including an input port and an output port in fluid communication with said reservoir;
   d. providing a rotary discharging mechanism housed within said casing;
   e. providing a controller electrically coupled to said reservoir for controlling an operating speed of said rotary discharging mechanism; and
   f. said liquid air freshening compound entering through said input port and traveling along a unidirectional arcuate path defined along a major interior circumference of said discharge casing prior to exiting through said output port;
   wherein step c. comprises the steps of:
   providing a hollow chamber formed within said casing;
   providing a rod rotatably disposed within said chamber;
   providing a mobile ring eccentrically disposed within said chamber, said mobile ring being provided with a plurality of linear fingers radially protruding outwardly from a perimeter thereof;
   providing a plurality of rectilinear levers directly attached to said rod and terminating the exterior of said mobile ring;
   providing a plurality of cranks pivotally attached to said fingers and said levers respectively; and
   providing a plurality of flaps pivotally coupled to said levers;
   a traveling force of said liquid air freshening compound causing said mobile ring and said fingers to eccentrically rotate about said rod;
   maintaining outer edges of said flaps directly engaged with an interior surface of said chamber; and
   propelling said liquid air freshening compound outward from said output port.

7. The method of claim 6, further comprising the step of: synchronously displacing said flaps within said chamber.

8. The method of claim 6, further comprising the step of: directly linking opposed ends of said cranks to corresponding ends of said levers and said fingers respectively.

9. The method of claim 6, further comprising the step of: extending each of said flaps from an outer perimeter of said mobile ring to said inner surface of said chamber.

10. The method of claim 6, further comprising the steps of: statically coupling said levers to said rod; and
maintaining a dynamic spatial relationship with said fingers when said mobile ring is eccentrically rotated about said rod for ensuring that said flaps maintain direct engagement with an inner surface of said chamber during rotary movement.

* * * * *